United States Patent [19]

Heiss

[11] Patent Number: 4,492,657
[45] Date of Patent: Jan. 8, 1985

[54] IMINES OF ALKYL 4-HALOMETHYLBENZOATES

[75] Inventor: Lorenz Heiss, Hofheim am Taunus, Fed. Rep. of Germany

[73] Assignee: Hoechst Aktiengesellschaft, Fed. Rep. of Germany

[21] Appl. No.: 488,126

[22] Filed: Apr. 25, 1983

[30] Foreign Application Priority Data

May 5, 1982 [DE]  Fed. Rep. of Germany ....... 3216722

[51] Int. Cl.³ ........................................... C07C 119/20
[52] U.S. Cl. .................................................. 260/453.7
[58] Field of Search ..................................... 260/453.7

[56] References Cited

U.S. PATENT DOCUMENTS 2,389,681  11/1945  Mikeska ........................... 260/453.7

Primary Examiner—Henry R. Jiles
Assistant Examiner—Robert C. Whittenbaugh
Attorney, Agent, or Firm—Connolly and Hutz

[57] ABSTRACT

New alkyl (4-halomethyl)iminobenzoates of the formula

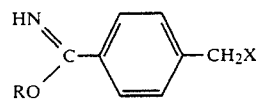

and their HCl or HBr salts, R denoting $C_1$-$C_4$-alkyl or $C_1$-$C_4$-alkoxyethyl and X denoting Cl or Br. These compounds are prepared by reaction of p-cyanobenzyl chloride or p-cyanobenzyl bromide with a $C_1$-$C_4$-alcohol or $C_1$-$C_4$-alkoxyethanol in the presence of hydrogen chloride or bromide. The new imines serve as intermediate products, inter alia for the preparation of optical brighteners of the bisbenzoxazolylstilbene class.

1 Claim, No Drawings

IMINES OF ALKYL 4-HALOMETHYLBENZOATES

The invention relates to new alkyl (4-halomethyl)iminobenzoates of the formula

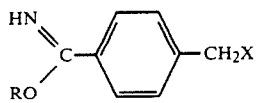

and their HCl or HBr salts, R denoting $C_1$–$C_4$-alkyl or $C_1$–$C_4$-alkoxyethyl and X denoting Cl or Br.

These compounds are prepared by reaction of p-cyanobenzyl chloride or p-cyanobenzyl bromide with a $C_1$–$C_4$-alcohol or $C_1$–$C_4$-alkoxyethanol in the presence of hydrogen chloride or bromide. The reaction is carried out such that 1 mole of p-cyanobenzyl halide is dispersed in an excess of about 1.5 to 5 moles of the alcohol and hydrogen chloride or hydrogen bromide is passed into this reaction mixture at a temperature from 0 to 30, preferably 5 to 20, °C. for about 10 to 30, preferably about 20, hours. The amount of hydrogen halide is not critical, but the equivalent amount is a minimum, and it is optimal to have an amount of 2 moles of hydrogen halide to one mole of cyanobenzyl halide. After completion of the reaction, the excess hydrogen halide is removed or neutralized and the excess of alcohol is distilled off. The alkyl (4-halogenomethyl)iminobenzoates are obtained in the form of their HCl or HBr salts. These salts can be immediately further processed. If it is desired to obtain the free alkyl ester imines, it is necessary, by known methods to react the salts with an equivalent amount of a base.

It is possible to prepare from these alkyl (4-halomethyl)iminobenzoates or their salts, by reaction with o-aminophenols, o-aminothiophenols or o-phenylenediamines, 2-benzoxazolyl-4-halomethylbenzenes and their thiazolyl and imidazolyl analogs. These latter compounds are valuable starting materials for the preparation of optical brighteners of the 4,4'-dioxazolyl-2-stilbene class (Khim. Geterozikl. Soedin Vol. 1981, 463–467) and for the preparation of compositions which are polymerized by UV radiation (U.S. Pat. No. 3,912,606) and of UV stabilizers (U.S. Pat. No. 4,075,162).

EXAMPLE 1

75.8 g (0.5 mole) of p-cyanobenzyl chloride are dispersed in 32 g (1 mole) of methanol and about 35.5 g (1 mole) of hydrogen chloride are passed in at 5°–15° C. The mixture is further stirred for about 20 hours until the nitrile band at 2,220 cm$^{-1}$ in the infrared spectrum has disappeared. After removing the methanol and hydrogen chloride, 110 g (0.5 mole) of methyl 4-chloromethylbenzimidate hydrochloride are obtained.

Yield: quantitative found: C: 49.0%; H: 5.0%; Cl: 32.0%; Cl$^-$: 16.1%;
calculated: C: 49.2%; H: 5.0%; Cl: 32.2%; Cl$^-$: 16.1%.

EXAMPLE 2

98 g (0.5 mole) of p-cyanobenzyl bromide are dispersed in 46 g (1 mole) of ethanol and about 32 g (0.9 mole) of hydrogen chloride are passed in at 20° to 25° C. The mixture is further stirred for about 18 hours until the nitrile band at 2,220 cm$^{-1}$ in the IR spectrum has disappeared. After removing the ethanol and hydrogen chloride, 139 g (0.5 mole) of ethyl 4-bromomethylbenzimidate hydrochloride are obtained.

Yield: quantitative.

found: C: 43.0%; H: 4.8%; Br: 28.2%; Cl$^-$: 12.5%;
calculated: C: 43.1%; H: 4.7%; Br: 28.7%; Cl$^-$: 12.7%.

I claim:

1. An alkyl (4-halomethyl)iminobenzoate of the formula

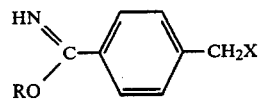

and its HCl or HBr salts, R denoting $C_1$–$C_4$-alkyl or $C_1$–$C_4$-alkoxymethyl and X denoting Cl or Br.

* * * * *